United States Patent [19]

Drouet et al.

[11] 4,154,821

[45] May 15, 1979

[54] NOVEL GLYCOPROTEINS

[75] Inventors: Jean-Claude Drouet, Luzarches; Marie-Odile Martin, Paris; Dominique Biard, Cergy; René Zalisz, Saint-Ouen L'Aumone, all of France

[73] Assignee: Roussel Uclaf, Paris, France

[21] Appl. No.: 871,408

[22] Filed: Jan. 23, 1978

[30] Foreign Application Priority Data

Jan. 27, 1977 [FR] France .................. 77 02267

[51] Int. Cl.$^2$ ............................................. A61K 37/00
[52] U.S. Cl. .................................... 424/177; 195/2; 195/4; 195/29; 260/112 R
[58] Field of Search .................. 195/2, 4, 29; 424/177

[56] References Cited

U.S. PATENT DOCUMENTS

| 3,616,453 | 10/1971 | Kawaji | 195/29 |
|---|---|---|---|
| 3,716,452 | 2/1973 | Kitamura et al. | 195/2 |
| 3,855,197 | 12/1974 | Hirsch et al. | 195/29 |
| 3,868,303 | 2/1975 | Tsumura et al. | 195/29 |
| 3,876,779 | 4/1975 | Adam et al. | 195/2 |
| 3,917,510 | 11/1975 | Kitamura et al. | 195/2 |
| 3,976,544 | 8/1976 | Adam et al. | 195/4 |
| 4,013,788 | 3/1977 | Jolles et al. | 424/177 |
| 4,032,663 | 6/1977 | Kobayashi et al. | 195/2 |
| 4,036,953 | 7/1977 | Adam et al. | 195/4 |

FOREIGN PATENT DOCUMENTS

| 1046770 | 5/1963 | United Kingdom | 195/2 |
|---|---|---|---|
| 1426042 | 2/1973 | United Kingdom | 195/2 |

OTHER PUBLICATIONS

S. Kotani, et al., Biken Journel, vol. 18, pp. 105–111, (1975).
F. Audibert, et al., Cellular Immunology 21, pp. 243–249, (1976).
A. Adam, et al., Biochem. and Biophys. Res. Comm. 72, 1976, pp. 339–346.
D. Perlman, Chem. Abst., vol, 84, 1976, 84764x.
Kotani, et al., Biken Journel, 18, 1975, pp. 77–92.

*Primary Examiner*—Delbert R. Phillips
*Attorney, Agent, or Firm*—Hammond & Littell

[57] ABSTRACT

Novel water-soluble glycoproteins isolated from Hafnia strain having remarkable anti-inflammatory and immunostimulating activity with very good tolerance and their preparation.

16 Claims, No Drawings

NOVEL GLYCOPROTEINS

STATE OF THE ART

Numerous preparation of microbial origin derived from lysis of microbial bodies are described in the literature such as French BSM No. 5488M, No. 6495M and No. 6513M. The microbial lysates, alone or associated with an antibiotic, serve to release a rapid immunization reaction or to increase the defenses of the organism against microbial aggression. Lysates generally proceed against a specific microbial species and lead to a specific or general immunization. They possess the disadvantage of being generally allergenic and their repeated use is not recommended.

French Pat. No. 2,043,475 describes a glycoprotein fraction isolated from one or more saprophyte or pathogenic strains that possesses an immunitary power and a certain anti-inflammatory action.

OBJECTS OF THE INVENTION

It is an object of the invention to provide a novel water-soluble glycoprotein derived from Hafnia strains and to a novel process for their preparation.

It is another object of the invention to provide novel anti-inflammatory and immunostimulating compositions and to a novel method of relieving inflammation in warm-blooded animals.

These and other objects and advantages of the invention will become obvious from the following detailed description.

THE INVENTION

The novel glycoproteins of the invention are comprised of water-soluble glycoproteins having anti-inflammatory and immunostimulating activity extracted from lyses of microbial bodies of Hafnia strain and having an apparent molecular weight of at least 300,000, preferably of 1,000,000 or more.

The apparent molecular weight is the molecular weight determined by the average of a porous gel calibrated with known macromolecular solutions. Among the calibrated porous gels used to determine molecular weight are the commercial gels sold under the trademark Sepharose, especially Sepharose 6B gels.

Among the glycoproteins of the invention are those containing 40 to 50% of biuretogenic substances and 25 to 35% of neutral sugars, contain no diaminopimelic acid and present an absorption maximum in ultraviolet at about 215 and 260 m$\mu$.

As substances having biuretogenic power are the proteins giving the colored reaction of biuret. As neutral sugars are the neutral hexoses as glucose, galactose or mannose. The absence of diaminopimelic acid in the glycoproteins indicates the non-membrane origin of the glycoproteins. The preferred glycoproteins are those extracted from the Hafnia strain filed in the Pasteur Institute in Paris under No. 5731 although other Hafnia strains may be used.

The novel process of the invention for the preparation of the novel water-soluble glycoproteins comprises cultivating a Hafnia microbial strain in a solid or liquid nutritive media until complete developement of the microbial bodies, collecting the said bodies, subjecting the latter to lysis, treating the resulting lysate with at least one organic solvent, dissolving the resulting product in water and subjecting the aqueous solution to diafiltration with a porous membrane calibrated having a threshold for retaining substances with a molecular weight of at least 300,000 and subjecting the resulting solution to lyophilis to obtain the water-soluble glycoprotein.

Preferably, the Hafnia strain is cultivated in a stirred liquid media under aerobic conditions. The culture medium used is a conventional media containing, for example, meat extracts, casein peptone, soybean papainic peptone, yeast autolysates, sugars, mineral elements and distilled water.

The lysis of the microbial bodies may be physical, chemical or enzymatic. Physical lysis is preferably effected with ultrasonic means or by heating or by penetrating radiation. Chemical lysis is preferably effected with adjunction of a surface active agent such as polyethyleneglycol sorbate or with an antiseptic organomercurial agent such as sodium mercuriothiolate and even with a mineral or organic acid such as trichloroacetic acid. Enzymatic lysis is preferably effected with an enzyme such as lysozyme, trypsin, pronase, papain or $\alpha$-chymotrypsin. The lysis, whether physical, chemical or enzymatic, is preferably 7 to 60 days long.

The lysate may be lyophilised.

The resulting lysate is treated with one or more organic solvents and preferably with at least two solvents in separate steps such as first acetone and then methanol. The said treatment is intended to eliminate lipids and pigments and in practice the mixtures of lysate and solvent are vigorously stirred for several hours.

The porous membranes calibrated to retain substances with a molecular weight equal to or greater than 300,000 are preferably commerical membranes sold by Romicon and Amicon under the designation XM 300. These membranes can occur in the form of hollow fibers and commercial hollow fibers of this type are sold by Amicon uner the designation HIP 100.

In a variation of the process of the invention, a preliminary diafiltration is effected with a porous membrane calibrated to retain only substances with a molecular weight less than 300,000. An example of a membrane suitable for this step are membranes capable of retaining substances with a molecular weight of 100,000 such as the commercial membranes of Amicon sold under the designation XM 100.

In a preferred mode of the process of the invention, the microbial strain in Hafnia No. 5,731, the lysis of the microbial bodies is an enzymatic lysis, preferably with lysozyme, the treatment of the lysate with organic solvents is effected with acetone and methanol successively and the porous membrane is the membrane sold under the mark XM 300.

The glycoproteins of the invention are slightly beige colored, odorless, neutral and water-soluble at a concentration of 25 mg/ml and are insoluble in solvents such as ethanol, methanol, acetone, ether or benzene. Chromatography over Sepharose 6B shows that the molecular weight of the products is greater than 1,000,000. The ultraviolet absorption spectrum shows an absorption of short wave lengths (maximum of about 215 m$\mu$) characteristic of a peptide bond and a weak absorption of about 260 m$\mu$ characteristic of nucleic acids and proteins. The infrared absorption spectrum confirms the peptidic part of the products. The characteristic reactions of sugars with orcinol and carbazole are positive and the characteristic reactions of peptidic bonds with biuret, Lowry and ninhydrin are also positive.

The glycoproteins of the invention of the application are not dialysable, are pharmacologically stable in the presence of heat (one hour at 105° C.) and at extreme pHs (pH 3 and 10–15 hours at 4° C.) and are resistant to proteolytic enzyme such as pronase (24 hours at 37° C.).

The novel anti-inflammatory and immunostimulating compositions of the invention which are very well tolerated are comprised of an anti-inflammatorily and immunostimulating effective amount of a glycoprotein of the invention and an inert pharmaceutical carrier or excipient. The compositions may be in the form of tablets, dragees, gelules, granules, solutions, syrups, suppositories, injectable suspensions or solutions, ovules, creams, pomades, lotions, drops or collyriums.

Examples of suitable excipients for the compositions are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

The compositions are useful for the treatment of inflammation of the skin, of mucous and like anti-pruriginous, in dermatology, in oto-rhino-laryngology, in ophthalmology, in proctology or in gynecology as well as in the treatment of chronic or acute intestinal infections such as colibacillosis, in the treatment of alimentary toxic infections of Salmonella and enterotoxic staphylococcus, in the treatment of dysenteric syndromes of microbial origin such as shigellosis, in the treatment of digestive candidosis and in the treatment of urinary infections of Proteus and Pseudomonas.

The novel method of the invention for relieving inflammation and inducing immunostimulating activity in warm-blooded animals, including humans, comprises administering to warm-blooded animals an effective amount of a glycoprotein of the invention. The said product may be administered locally, orally, rectally or parenterally and the usual effective does is 0,001 to 1 mg/kg depending on the method of administration.

In the following examples there are described several preferred embodiments to illustrate the invention. However, it should be understood that the invention is not intended to be limited to the specific embodiments.

EXAMPLE 1

STEP A: culture

A culture medium was prepared by successively mixing into about 20 liters of distilled water 690 g of meat extract, 690 g of sodium chloride, 690 g of casein peptone, 690 g of yeast autolysate, 483 g of dipotassium phosphate, 207 g of monopotassium phosphate and the pH of the resulting solution was adjusted to about 7. The medium was sterilized at 120° C. for 40 minutes and then a solution of 4104 g of glucose and 2760 g of soybean papainic peptone was added to the culture medium at the moment of seeding after having first been sterilized. The Hafnia strain (Pasteur Institute No. 5731) to be cultivated in the gelose media was added to 50 ml of the culture media and this solution acting as the inoculum was added to the rest of the culture bouillon and the total volume of the culture medium was adjusted to 138 liters by the addition of sterile distilled water.

The culture medium was held at 37° C. and the pH was automatically adjusted to 7 by addition of hydrochloric acid solution or ammonium hydroxide solution. The increase in germs was determined photometrically to calculate the number of germs as the function of the optical density determined by comparison with a standard curve. After complete development or after about 7 hours, the medium contained about 1,000,000,000 germs per ml.

STEP B: lysis:

An aqueous solution of lysozyme hydrochloride (sterilized by filtration through an 0.22 $\mu$ millipore membrane) was added to 138 liters of the culture of Step A to obtain in final concentration of 160 $\gamma$ of lysozyme hydrochloride per ml of culture and the mixture remained in contact at 56° C. in the presence of 0.25 g of EDTA, 862.5 mg of sodium mercurothiolate and 80 g of polysorbate (Tween 80) per liter of culture bouillon. The lysis was continued for 7 days at 37° C. under sterile conditions and the resulting lysate was homogenized by stirring and was lyophilized to obtain 7900 g of a brown powder.

STEP C: Treatment

The brown powder from Step B was suspended in 138 liters of cold acetone and the suspension was vigorously stirred for 3 hours at 3500 rpm and was then filtered through a glass frit. The mixture was rapidly vacuum filtered to obtain 7295 g of a yellow powder which was suspended in 138 liters of cold methanol. The mixture was vigorously stirred for 3 hours at 1500 rpm and the mixture was then decanted. The major part of the surnagent was drawn off with a siphon and the rest was filtered through a glass frit. The powder was vacuum filtered and dried at room temperature under reduced pressure for 24 hours to obtain 3988 g of a clear beige powder.

STEP D: Diafiltration 3600 g of the powder of Step C was dissolved in 60 liters of distilled water containing 1 g/l of merthiolate and the solution was stirred at 4° C. for 24 hours and was then centrifuged for 2 hours at 4000 rpm and then was added to a continuous centrifuge at 90,000 g at a range of 6 liters per hour and the recovered solution was adjusted to a volume of 10 liters with distilled water filtered through a 0.22 $\mu$ millipore membrane. The solution was introduced into diafilter apparatus equipped with porous membranes with a retention threshold of 300,000 and an apparent diameter of the pores being approximately 2Å (commerical membranes of Amicon sold under the mark XM 300). 50 volumes of distilled water (500 liters) were circulated through the apparatus for about 48 hours and the diafiltration solution was then placed in a continuous centrifuge at 90,000 g at a rate of 6 liters per hour. 9.5 liters of solution was obtained which was then lyophilized to obtain 105 g of glycoproteins in the form of a cottony white-beige powder which was very hygroscopic.

Analysis: %C 37.9; %H 6; %N 7.5. Content: 9% water; 0.01% phosphorus; 0% chlorine; proteins—51% biuret; sugars—29% orcinol (neutral hexoses) and 1.5% carbazole (uronic acids). U.V. Spectrum: max. at 216 m$\mu$ and 258 m$\mu$. I.R. Spectrum: confirmed the nature of peptidic part of the products.

Hydrolysis of the glycoprotein product with 6N hydrochloric acid at 110° C. for 24 hours followed by chromatography over a cellulose plate with one of the following solvent systems: 60-30-30 n-butanol-acetic acid-water mixture, 2-1 isopropanol-ammonium hydroxide mixture or 18-50-4-28 methanol-pyridine-acetice acid-water mixture showed the absence of diaminopimelic acid in the hydrolysates indicating the non-membranic origin of the glycoproteins.

The study of the curve of the optical densities at 280 m$\mu$ of the eluate of chromatography of the glycoprotein over Sepharose 6B as a function of Ve/Vo showed a molecular weight greater than 1,000,000. Vo is the elution volume of a dextran with a molecular weight greater than 1,000,000 totally excluded on Sepharose 6B whose limiting molecular weight of exclusion is 1,000,000 and Ve corresponds to the elution volume of Hafnia glycoproteins.

EXAMPLE 2

90 liters of lysate were obtained as in Steps A and B of Example 1 and the lysate was lyophilized to obtain 4570g of a yellow-brown powder. The said powder was extracted with 90 liters of cold acetone and 90 liters of cold methanol as in Step C of Example 1 and the product was dried under reduced pressure to obtain 1765 g of a beige powder.

600 g of the said powder were suspended in 15 liters of distilled water and the suspension was stirred at 4° C. for 15 hours. The solution was then centrifuged at 4000 rpm for 2 hours and was then passed through a continuous centrifuge at 90,000 g and a feed rate of 6 liters per hour to obtain 14 liters of solution. The latter was introduced into a diafiltration apparatus equipped with XM 300 membranes and the solution was washed with 40 volumes of distilled water for about 48 hours. The final solution was centrifuged at 90,000 g and was then lyophilized to obtain 55.6 g of the cottony white-beige powder which was very hygroscopic.

Analysis: %C 40.3; %H 6; %N 8.3. Content: 10% water; 0.025% phosphorus; 0% chlorine; proteins—41% biuret; sugars—26% orcinol (neutral hexoses). U.V. Spectrum: maximum at 215 m$\mu$ and 257 m$\mu$.
I.R. spectrum confirmed the nature of the peptidic part of the product-Diaminopimetic acid was absent and the molecular weight over Sepharose 6B was greater than 1,000,000.

EXAMPLE 3

Tablets were prepared containing 5 mg of the glycoproteins of Example 1 and sufficient excipient of lactose, talc, starch and magnesium stearate to obtain a final weight of 200 mg.

A pomade was prepared containing 200 mg of the glycoprotein of Example 2 and sufficient excipient to obtain 100 g of pomade.

PHARMACOLOGICAL STUDY

A. Anti-inflammatory Activity

The anti-inflammatory activity was determined on male rats by the technique of edema caused by carraghenine [Winter et al, Proc. Soc. Exp. Biol. Med., Vol. III (1961), p. 544–547]. The rats received in the tibio-tarsien articulation of a rear paw 0.05 ml of a suspension of 1% carraghenine. The test products were intraperitoneally administered at doses of 10$\gamma$ and 100$\gamma$/kg one hour before the carraghenine injection. The volume of the paw was measured with a plethysmometer before and 3 hours after the carraghenine injection and the results were expressed as a percentage of edema regression as a compared to the controls and are reported in Table I.

TABLE I

| Product of Example | Dose in $\gamma$/kg | % diminution of edema |
|---|---|---|
| 1 | 10 | 64 |
|   | 100 | 79.5 |
| 2 | 10 | 59 |

TABLE I-continued

| Product of Example | Dose in $\gamma$/kg | % diminution of edema |
|---|---|---|
|   | 100 | 75 | b. Modification of the cellular number

The glycoproteins of Example 1 were intraperitoneally administered to groups of guinea pigs at a dose of 50$\gamma$ or 100$\gamma$ per kg and the number of peritoneal cells was determined 48 hours after the injections. The number of cells compared to those of animals who did not receive the material shows that the glycoproteins did not cause modification of the cellular number.

C. Tolerance study

The glycoproteins of Examples 1 and 2 were subcutaneously administered to mice at doses of 250$\gamma$ and 1000$\gamma$ per kg in a volume of 0.2ml and they did not provoke any local or general Klebsiella There were no signs of inflammation in the subcutaneous tissue.

D. General preventive antibacterial activity

The glyproteins of Examples 1 and 2 were intraperitoneally administered to groups of 20 mice at doses of 1000$\gamma$ and 5000$\gamma$ per kg for six days and 48 hours before intraperitoneal injection with klebsiella Pneumonia corresponding to 100 and 500 times the DL$_{50}$ dose (50% of mice killed). The mortality was determined 7 days after the injection of the germs and was compared with a control group of mice receiving only physiological serum. The results are reported in Table II as the percentage of protection of treated animals.

TABLE II

| Product of Example | Dose in $\gamma$/kg | % Protection 100 + DL$_{50}$ | % Protection 500 + DL$_{50}$ |
|---|---|---|---|
| 1 | 1000 | 40 | 70 |
|   | 5000 | 40 | 20 |
| 2 | 1000 | 40 | 70 |
|   | 5000 | 40 | 20 |

E. Stimulation of non-specific defenses

The stimulation was studied with the carbon clearance test on mice inspired by the technique of Halpern [C.R. Soc. Biol., Vol. 148 (1954), p. 431]. The stimulation was shown by the increase of phagocytair activity 30 minutes after the peritoneal injection of the glycoproteins of Examples 1 and 2. At the dose of 250$\gamma$/kg, the increase was 77.5% and 88% for the products of Examples 1 and 2, respectively and at 100$\gamma$/kg the increase was 31% and 86%, respectively.

F. Evolution of weight rate

Two intraperitoneal injections of the products of Examples 1 and 2 mice at 48 hours intervals at a dose of 100$\gamma$,250$\gamma$and 500$\gamma$/kg did not have any significant effect on the weight rate.

G. Acute toxicity

The acute toxicity of the product of Example 1 was determined by the method of Behrens and Karber on mice receiving the product intraperitoneally and the DL$_{50}$ dose was 50 mg/kg.

Various modifications of the proucts and process of the invention may be made without departing from the spirit or scope thereof and it is to be understood that the invention is intended to be limited only as defined in the appended claims.

We claim:

1. A water-soluble glycoprotein extracted from the lysis of microbial bodies of Hafnia and having an apparent molecular weight of at least 300,000.

2. The glycoprotein of claim 1 wherein the apparent molecular weight of at least 1,000,000.

3. The glycoprotein of claim 1 containing 40 to 50% by weight of substances with biuretogenic power, 25 to 35% by weight of neutral sugars, no diaminopimelic acid and has an ultraviolet absorption maximum at about 215 mµ and 260 mµ.

4. The glycoprotein of claim 1 wherein the Hafnia strain is No. 5731 of Pasteur Institute of Paris.

5. A process for the preparation of a glycoprotein of claim 1 comprising cultivating a Hafnia microbial strain in a solid or liquid nutritive media until complete developement of the microbial bodies, collecting the said bodies, subjecting the latter to lysis, treating the resulting lysate with at least one organic solvent, dissolving the resulting product in water and subjecting the aqueous solution to diafiltration with a porous membrane calibrate having a threshold for retaining substances with a molecular weight of at least 300,000 and subjecting the resulting solution to lyophilis to obtain the water-soluble glycoprotein.

6. The process of claim 1 wherein the lysis is an enzymatic lysis, and the lysate is treated successively with acetone and methanol.

7. The process of claim 6 wherein the enzymatic lysis effected with lysozyme.

8. The process of claim 5 wherein the Hafnia strain is No. 5731 of the Pasteur Institute of Paris.

9. Pharmaceutical composition containing an anti-inflammatorily and immunostimulating effective amount of a glycoprotein of claim 1 and an inert pharmaceutical carrier.

10. The composition of claim 9 wherein the apparent molecular weight of the glycoprotein is at least of 1,000,000.

11. The composition of claim 9 containing 40 to 50% by weight of substances with biuretogenic power, 25 to 35% by weight of neutral sugars, no diaminopimedic acid and has an ultraviolet absorption maximum at about 215 mµ and 260 mµ.

12. The composition of claim 9 wherein the Hafnia strain is No. 5731 of Pasteur Institute of Paris.

13. A method of relieving inflammation and inducing immunostimulating activity in warm-blooded animals comprising administering to warm-blooded animals an anti-inflammatorilly and immunostimulating amount of a glycoprotein of claim 1.

14. The method of claim 13 wherein the apparent molecular weight is at least of 1,000,000.

15. The method of claim 13 containing 40 to 50% by weight of substances with biuretogenic power, 25 to 35% by weight of neutral sugars, no diaminopimelic acid and has an ultraviolet absorption maximum at about 215 mµ and 260 mµ.

16. The method of claim 13 wherein the Hafnia strain is No. 5731 of Pasteur Institute of Paris.

* * * * *